United States Patent
Xin et al.

(10) Patent No.: US 7,649,624 B1
(45) Date of Patent: Jan. 19, 2010

(54) SYSTEMS AND METHODS FOR DETECTING SCRATCHES ON NON-SEMICONDUCTOR WAFER SURFACES

(75) Inventors: Yun-Biao Xin, Palo Alto, CA (US); Martin Andrew Smith, San Jose, CA (US); Ronald Charles Dwelle, Sunnyvale, CA (US); Gerard Vurens, Palo Alto, CA (US)

(73) Assignee: Crystal Technology, Inc., Palo Alto, CA (US)

( * ) Notice: Subject to any disclaimer, the term of this patent is extended or adjusted under 35 U.S.C. 154(b) by 6 days.

(21) Appl. No.: 12/174,004

(22) Filed: Jul. 16, 2008

(51) Int. Cl.
  *G01N 21/00* (2006.01)
(52) U.S. Cl. .................. 356/237.2; 356/237.5
(58) Field of Classification Search .... 356/237.1–237.5
  See application file for complete search history.

(56) References Cited

U.S. PATENT DOCUMENTS

| | | | |
|---|---|---|---|
| 5,965,896 A * | 10/1999 | Marton | 250/559.4 |
| 2007/0081150 A1* | 4/2007 | Leonard et al. | 356/237.2 |
| 2007/0121107 A1* | 5/2007 | Tsai et al. | 356/237.2 |
| 2009/0116753 A1* | 5/2009 | Midgley et al. | 382/219 |

* cited by examiner

*Primary Examiner*—Hoa Q Pham
(74) *Attorney, Agent, or Firm*—Paul Davis; Goodwin Procter LLP

(57) ABSTRACT

A method of detecting one or more scratches on a surface of a wafer made of a non-semiconductor material is provided. A UV beam is produced from a UV illumination source. The UV beam is incident on a front surface of the wafer. The UV beam being characterized that for scratches of a given material having a UV cutoff wavelength $\lambda_{cutoff}$, over 90% of the spectral system response SSR is at wavelengths below $\mu_{cutoff}$–5 nm and expressed as:

$$\int_0^{\lambda_{cutoff}-5nm} SSR(\lambda) > 0.90 \cdot \int_0^{\infty} SSR(\lambda)$$

A reflected beam of scattering of the UV beam is detected in response to scratches on a surface of the wafer. The scattering is captured.

29 Claims, 4 Drawing Sheets

Wavelength (nm)

SYSTEMS AND METHODS FOR DETECTING SCRATCHES ON NON-SEMICONDUCTOR WAFER SURFACES

BACKGROUND OF THE INVENTION

1. Field of the Invention

This invention relates generally to systems and methods for detecting scratches on surfaces of wafers, and more particularly to systems and methods for detecting scratches on surfaces of wafers made of non-semiconductor materials.

2. Description of the Related Art

With the reduction of design feature size and elevation of device reliability standards, the device manufacturer has imposed an increasing demand for better substrate surface quality, calling especially for the elimination of scratch defects. The device manufacturer is now requiring that substrates be free of polished surface scratches at the device application level. This requirement is well beyond our current inspection capability for scratch defect detection. To meet this quality control requirement, it is imperative for substrate manufacturers to possess/develop the ability to detect scratch defects in a more effective and efficient manner while also accommodating production output increases.

The objective of the invention is to develop an inspection system with much higher sensitivity in detecting scratch defects than what is visible when using the high-intensity light, un-aided eye visual inspection technique. Additionally, the invention will significantly improve upon the throughput limitations experienced when using commercial laser inspection systems, such as the Candela CS2 product.

Currently, visual and laser scanning are two methods used when inspecting for polished surface scratches. Neither of these methods is effective in capturing subtle scratch defects.

With visual inspection, a skillful technician holds a wafer under illuminating light in a dark room and/or surrounding to determine if a scratch is present on the wafer surface. This is achieved based on scattering from the scratch as the wafer is tilted at an angle of incidence to the light. However, the visual inspection method has three main drawbacks, (i) Poor capture rate: This is due to the transmission nature of lithium niobate wafer under visual light. Scattering from backsides' rough surface confounds the scatter from the scratch on the front surface, thereby greatly reducing the sensitivity of scattering from a scratch;

(ii) Inconsistency: The inspection ability is highly skill-dependent;

(iii) Labor intensive: It is direct labor involved for each wafer inspection.

To achieve a high capture rate, a laser inspection system based on low incidence angle is generally deployed. It does offer the ability to capture the scratch under submicron. However, due to the smaller laser beam size (5~50 um), the inspection throughput is too low to meet the production volume demands. High operation cost together with a steep initial capital investment commitment has prohibited the system from being used 100% for scratch screening in production, especially in the case where the fabrication cost of substrates is very competitive.

The current scratch detection methods available are either not effective as required or are cost prohibitive. Accordingly, there is a need for an effective and efficient inspection method at a reasonable investment cost.

SUMMARY OF THE INVENTION

An object of the present invention is to provide systems and methods for detecting scratches on surfaces of non-semiconductor material wafers.

These and other objects of the present invention are achieved in, a method of detecting one or more scratches on a surface of a wafer made of a non-semiconductor material. A UV beam is produced from a UV source. The UV beam being characterized that for scratches of a given material having a UV cutoff wavelength $\lambda_{cutoff}$, over 90% of the spectral system response SSR is at wavelengths below $\lambda_{cutoff}-5$ nm and expressed as:

$$\int_0^{\lambda_{cutoff}-5nm} SSR(\lambda) > 0.90 \cdot \int_0^{\infty} SSR(\lambda)$$

The UV beam is incident on a front surface of the wafer. A reflected beam of scattering of the UV beam is detected in response to scratches on a surface of the wafer. The scattering is captured.

In another embodiment of the present invention, a system is provided for detecting scratch on a surface of a wafer made of a non-semiconductor material. A UV source is provided that produces an output beam. The UV beam being characterized that for scratches of a given material having a UV cutoff wavelength $\lambda_{cutoff}$, over 90% of the spectral system response SSR is at wavelengths below $\lambda_{cutoff}-5$ nm and expressed as:

$$\int_0^{\lambda_{cutoff}-5nm} SSR(\lambda) > 0.90 \cdot \int_0^{\infty} SSR(\lambda)$$

A filter is positioned between the UV source and a target wafer made of a non-semiconductor material. The UV output beam has a diameter equal to at least ½ of a surface area of the wafer. A conversion lens, a beam stop and a screen or camera are provided.

In another embodiment of the present invention, a system for detecting scratch on a surface of a wafer made of a non-semiconductor material has a UV source that produces an output beam. The UV beam being characterized that for scratches of a given material having a UV cutoff wavelength $\lambda_{cutoff}$, over 90% of the spectral system response SSR is at wavelengths below $\lambda_{cutoff}-5$ nm and expressed as:

$$\int_0^{\lambda_{cutoff}-5nm} SSR(\lambda) > 0.90 \cdot \int_0^{\infty} SSR(\lambda)$$

The UV output beam has a diameter equal to at least ½ of a surface area of the wafer. A UV image lens is positioned in a front position relative to a UV camera. A filter is positioned between the UV source and the camera.

DETAILED DESCRIPTION OF THE PREFERRED EMBODIMENTS

Figure 1:
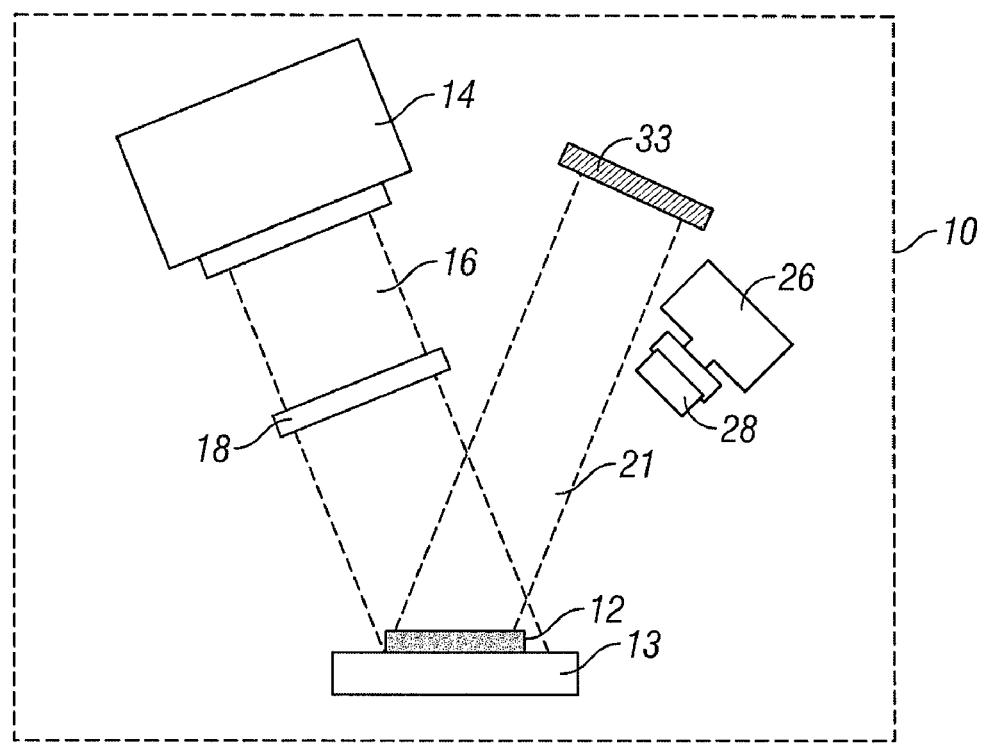
FIG. 1 illustrates one embodiment of a system for detecting scratches on a surface of a wafer of the present invention.

As illustrated in FIG. 1, one embodiment of the present invention is a system for detecting scratches on a surface of a wafer, generally denoted as element 10. The wafer 12 is made of a non-semiconductor material. In various embodiments, the non-semiconductor material is selected from, a piezo-electric material, an acousto-optic material, a material with a UV cut-off in the range of 250 nm to 350 nm and the like. As a non-limiting example, the material can be TeO2, sapphire, LN, LT, LBO, alpha quartz and the like. The wafers 12 can be of various sizes. In one embodiment, the wafers 12 are in the range of 100-200 mm.

A UV source 14 produces an output beam 16 in the wavelength region as defined below. In one embodiment, the output beam 16 is in the wavelength range of 250 to 300 nm. The UV illumination source 14 can be a mercury high pressure lamp.

The output beam 16 is absorbed by the bulk material of the wafer 12. The scattering is in response to scratches on a front surface of the wafer 12 that faces the UV beam, regardless of conditions on the wafer's back surface that faces away from the UV beam.

The output beam 16 can have a diameter that fully or partially illuminates the surface of the wafer 12. In one embodiment, the UV output beam 16 is sized so that it covers at least ½ of a surface area of the wafer 12.

In one embodiment, the image data acquisition and processing for scattering due to the scratches is done in a time period of less than 30 seconds. In another embodiment, it is done in a time period of about less than 30 seconds and more than a sub-second. The output beam 16 can have a diameter suitable for data acquisition and processing in the less than 30 second time period. In this manner, the output beam diameter is not so small that the number of illuminations required, due to a small beam diameter, causes the data acquisition and processing to exceed 30 seconds.

Figure 2:
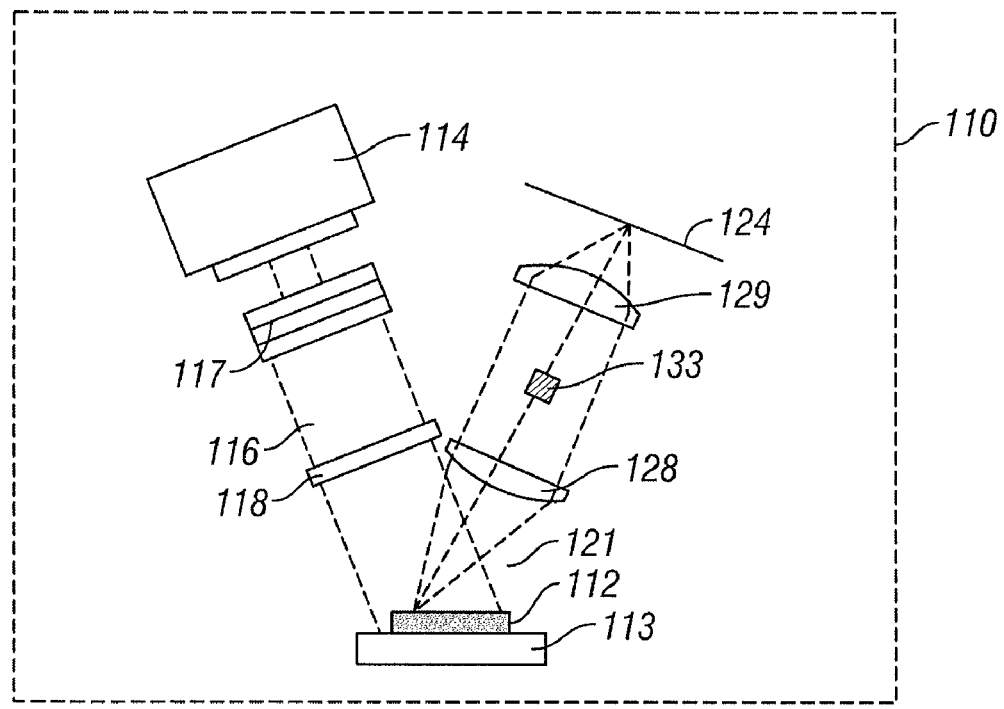
FIG. 2 illustrates another embodiment of a system for detecting scratches on a surface of a wafer of the present invention.

A screen 124, illustrated in FIG. 2, or a camera 26 are provided. In one embodiment, the imaging lens 28 and camera 26 are positioned such that the reflected beam 21 is not imaged. The beam 21 is caused by specular reflection of the incident beam 16 at the polished surface of wafer 12. In one embodiment, a beam stop 33 is provided. The beam stop 33 captures the reflected beam 21 and ensures it does not interfere with detection of scattered light from scratch of wafer 12. In one embodiment, multiple cameras 26 are provided in order to capture multiple angles of incidence. This is desirable because a scratch may be more visible in one angle compared to another. In one embodiment, the screen 124 is a fluorescent screen. A UV image lens 28 is positioned in a front position relative to the UV camera 26. The image lens 28 can be incorporated with the camera 26.

A filter 18 is positioned between the UV source 14 and the camera 26. In one embodiment, the filter 18 is positioned between the UV source 14 and the wafer 12.

As illustrated in FIG. 1, the system 10 can also include a wafer chuck 28. The wafer chuck 28 is configured to hold the wafer 12 in a manner so that it can be rotated, tilted and the like, in order to position the wafer 12 at different orientations. The wafer chuck 28 enables illumination at these orientations in order to see scratches at different angles of incidence. The output beam 16 is not scanned.

In another embodiment, illustrated in FIG. 2, a system 110 is provided for detecting scratch on a surface of a wafer 112 made of a non-semiconductor material. As in FIG. 1, the wafer 112 can be coupled to a wafer chuck 113. A UV source 114 provides an output beam 116 with the same wavelengths as in FIG. 1. Beam shaping optics 117 can be provided. The UV illumination source 114 can be a well focused mercury high pressure lamp or a UV laser. In one embodiment, the filter 118 is provided and cuts out visible and near UV radiation. The filter 118 is positioned between the UV source 114 and the screen 124 or camera 120. In one embodiment, the filter 118 is positioned between the UV source 114 and the wafer 112. In another embodiment, the UV source 114 has little spectral output at wavelengths longer than the UV cutoff wavelength of the wafer material 112, and the filter 118 can be omitted. In one embodiment, the lenses 128 and 129 form an imaging system that images the wafer surface onto the camera focal plane 126 or screen 124. A beam stop is provided at the focal point of UV lens 128 and it prevents the light beam 121 caused by the specular reflection from reaching the camera or screen. In another embodiment, the lens 129 is absent and the imaging is performed by lens 128 only.

In one embodiment, the scattering is observed or captured at an angle of 30~80 degree from the front surface of the wafer 112. In this embodiment, only forward scattering is detected. The image lens gathers the scattering which is then directed to the screen 124 or camera 26.

To analyze the spectral response of inspection system 10, all the individual components of the imaging system are reviewed. The same analysis applies to system 110. The UV source 14 can be a laser, LED, or a lamp emitting a portion of the power output as UV radiation. The optical power generated is characterized by the spectral power density function, $P(\lambda)$ measured in W/nm. As a non-limiting example, the spectral power density is shown for a high-pressure mercury discharge lamp with total output power of 100 W in FIG. 3.

Figure 4:
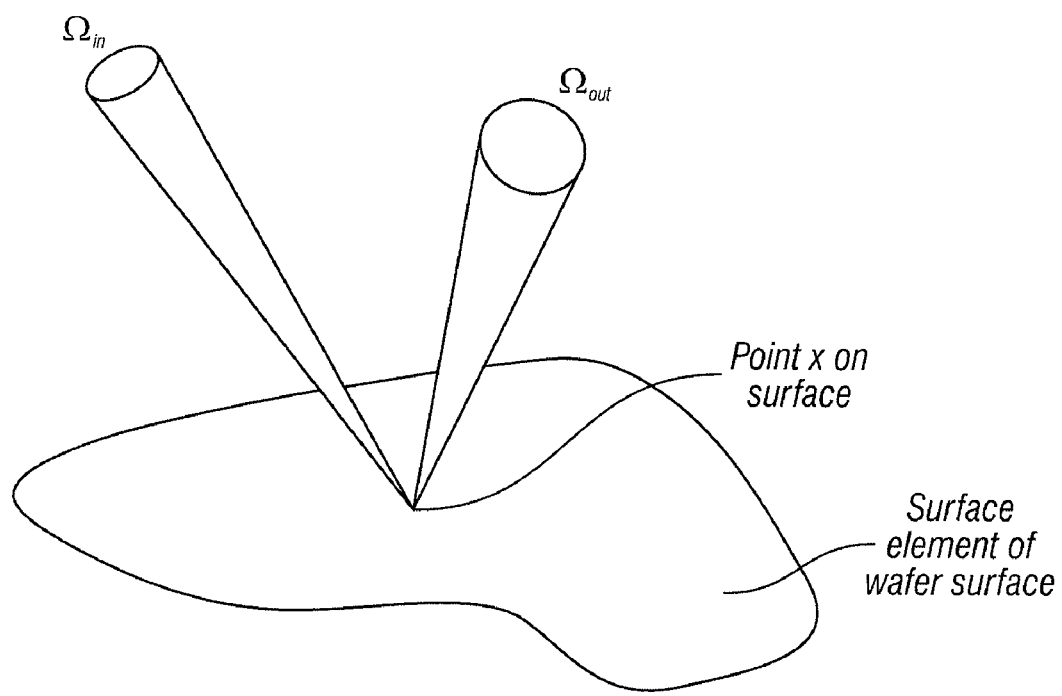
FIG. 4 defines the symbols used to describe the intensity of the beam as a function of location on the surface of a wafer 12 and the incident light direction.

The system 10 directs the optical power from the UV source 14 towards the surface of the wafer 12. At each location of the wafer 12, the spectral intensity falling onto the surface of the wafer 12 is defined by the source and imaging system. FIG. 4 defines the symbols used to describe the intensity as a function of location on the surface of the wafer 12 and the incident light direction. The location on the surface of the wafer 12, specified by x, is illuminated by the UV source 14, including the illumination imaging system. The spectral intensity at this location is given by the integration over all incident angles of the intensity distribution $I_{in}(x, \lambda, \Omega_{in})$. The intensity distribution is fairly uniform across the surface of the wafer 12 and peaks at solid angle directions $\Omega_{in}$ where the UV source 14 is located. The illumination system is characterized by a linear illumination function $I_{in}(x, \lambda, \Omega_{in}) = f_{in}(x, \lambda,$ $\Omega_{in}) \cdot P(\lambda)$ that depends on location to be illuminated, wavelength, and direction of illumination. The geometrical attributes of the illumination system such as aperture sizes, lens curvatures, beam stop, mirror contours and the like, predominantly determine where the light falls and from which direction it comes. The optical absorption and transmission characteristics predominantly determine the spectral characteristics. With this assumption, the illumination function $f_{in}$ can be factorized into two components, one describing the geometrical illumination characteristics that would result from perfectly clear optics having zero reflectivity (or perfect reflective mirror surfaces), and the other describing the spectral attenuation due to non-ideal optics and color filters inserted into the illumination path. This can express this as:

$$f_{in}(x, \lambda, \Omega_{in}) = g_{in}(x, \Omega_{in}) \cdot t_{in}(\lambda)$$

where the function $t_{in}(\lambda)$ ranges from 0 to 1 and describes the attenuation for particular wavelengths. It can be calculated by multiplying the spectral transmissivity of the various optical elements in the imaging system. This approximation is not generally true as aberrations in the illumination optics cause a slight wavelength-dependence across the surface of the wafer 12. It is, however, always possible to define a spectral attenuation function $t_{in}(\lambda)$ for the center of the wafer 12 and solid angle where the illumination peaks. This function is acceptably accurate for the purpose of the present invention.

A significant fraction of incident light is reflected at the surface of the wafer 12 in specular fashion and will be emitted into a small range of solid angles $\Omega_{out}$. The scratches and defects to be imaged emit scattered light into a larger range of solid angles, though at smaller intensity. This scattering can be described by the scattering function X that transforms the incoming illumination $I_{in}$ into the scattered light intensity $I_{out}(x, \lambda, \Omega_{out}) = X(x, \lambda, \Omega_{in}, \Omega_{out}) \cdot I_{in}(x, \lambda, \Omega_{in})$. The function X depends on the surface condition of the wafer 12 under investigation and is not subject to system design parameters.

Figure 5A:
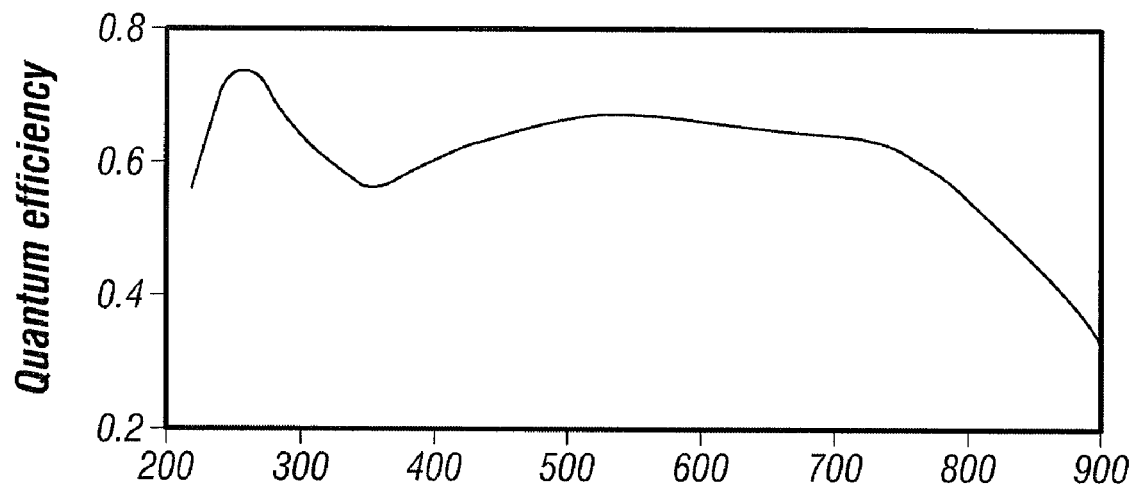
FIGS. 5(a) and 5(b) are graphs that illustrate the conversion of the probability of collecting an electron from a pixel when a photon of a particular wavelength strikes it, and the conversion is converted to a spectral response to intensity by dividing the quantum efficiency by the photon energy hv and multiplying with the electron charge.
Figure 5B:
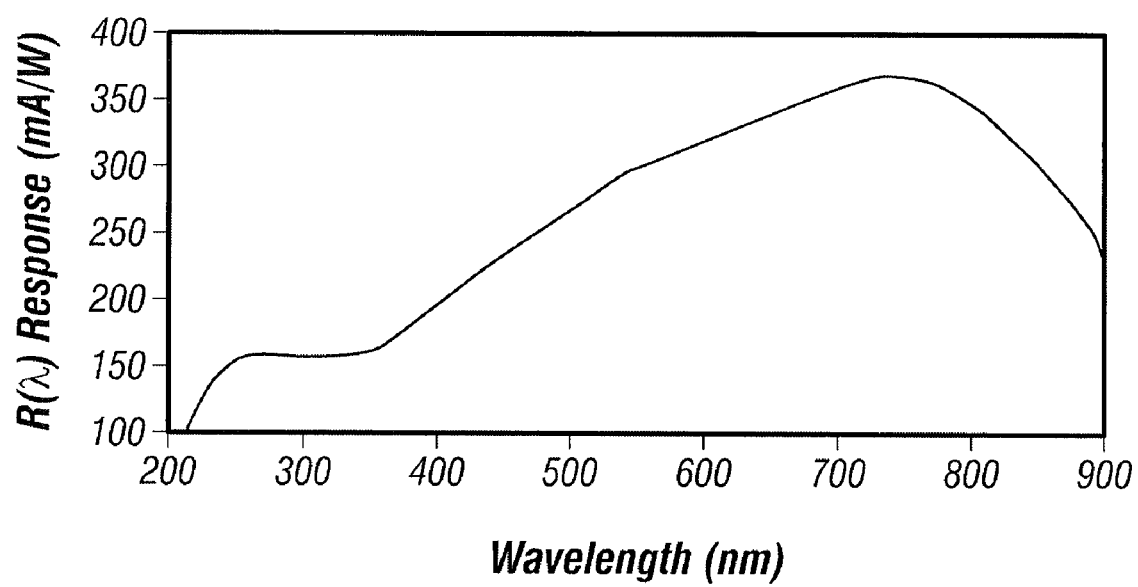

The light scattered or reflected off the surface of the wafer 12 is imaged by the detection system which consists of means to block most of the specular reflection and to collect the light scattered at the wafer surface. The light is imaged onto a screen 24 or camera 26 where each location (pixel) corresponds to a location on the surface of the wafer 12. The camera spectral sensitivity typically is given in units of quantum efficiency, i.e. the probability of collecting an electron from a pixel when a photon of a particular wavelength strikes it. This is converted into a spectral response to intensity by dividing the quantum efficiency by the photon energy hv and multiplying with the electron charge. FIGS. 5(a) and 5(b) show an example for a CMOS camera "MicroVista" by Intevac Inc. Santa Clara, Calif. 95054. The optical system imaging the scattered light from the surface of the wafer 12 onto the camera 26 can be treated in analog fashion to the illumination system. Let $R(\lambda)$ be the spectral response of the camera 26 that defines how much current a pixel produces for a given intensity at a particular wavelength. The imaging system that projects the scattered light $I_{out}(x, \lambda, \Omega_{out})$ onto a camera sensor is described in a similar fashion as that for the illumination function g:

$$\text{Camera intensity}(x, \lambda) = f_{out}(x, \Omega_{out}) \cdot t_{out}(\lambda) \cdot I_{out}(x, \lambda, \Omega_{out})$$

A complete description is now provided to characterize the spectral response of the apparatus including UV source 14, imaging systems illuminating the wafer 12 as well as imaging the surface onto the detector, and the camera. For a given location x on the surface of the wafer 12, the signal registered by the camera is given by $$\text{Signal}(x) = \int_0^\infty d\lambda \oint d\Omega_{in} \oint d\Omega_{out} R(\lambda) \cdot g_{in}(x, d\Omega_{in}) \cdot g_{out}(x, d\Omega_{in}) \cdot t_{in}(\lambda) \cdot t_{out}(\lambda) \cdot X(x, \lambda, d\Omega_{in}, d\Omega_{out}) \cdot P(\lambda)$$

This expression can be re-written as $$\text{Signal}(x) = \int_0^\infty d\lambda \cdot t_{in}(\lambda) \cdot t_{out}(\lambda) \cdot R(\lambda) \cdot P(\lambda) \times \oint d\Omega_{in} \oint d\Omega_{out} g_{in}(x, d\Omega_{in}) \cdot g_{out}(x, d\Omega_{in}) \cdot X(x, \lambda, d\Omega_{in}, d\Omega_{out})$$

The integral over the solid angles depend the geometrical characteristics of the system 10 and the defect scattering at the surface of the wafer 12. The factor $t_{in} \cdot t_{out} \cdot R \cdot P$ depends only on wavelength and is determined by the spectral response of the components selected. In this example, the spectral system response is defined as $SSR(\lambda) = t_{in}(\lambda) \cdot t_{out}(\lambda) \cdot R(\lambda) \cdot P(\lambda)$. In one embodiment of the present invention, the spectral system response is matched to that of the material to be inspected.

Figure 3:
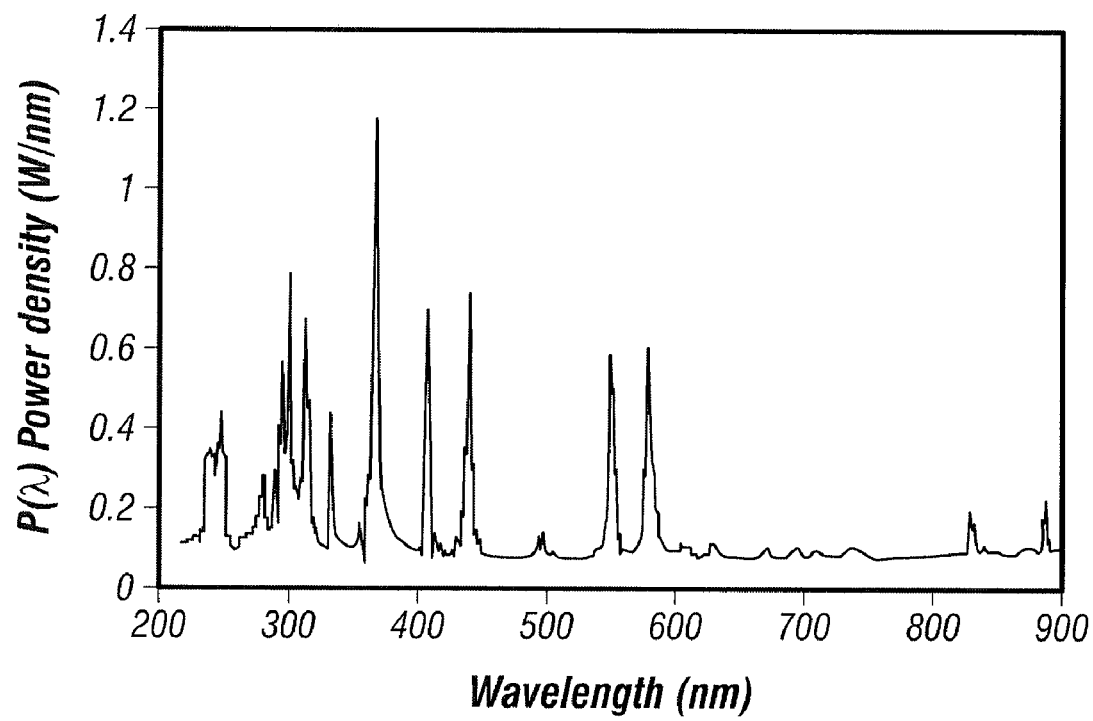
FIG. 3 is a graph that illustrates the spectral power density for a high-pressure mercury discharge lamp with total output power of 100 W.
Figure 6A:
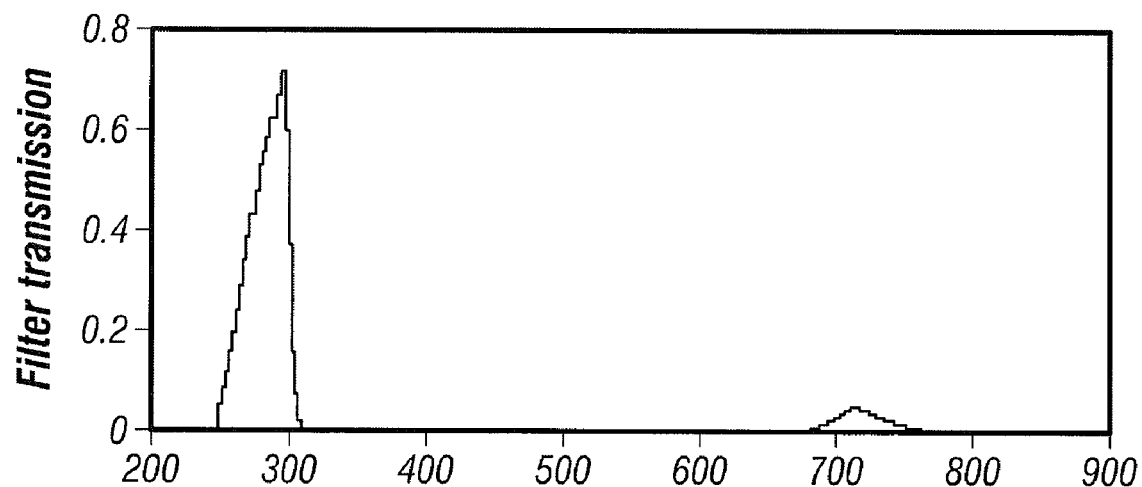
FIGS. 6(a) and 6(b) are graphs that illustrate the illumination response $t_{in}(\lambda)$ for thin film reflective filters, inserted in the illumination path, along with the spectral system response SSR.
Figure 6B:
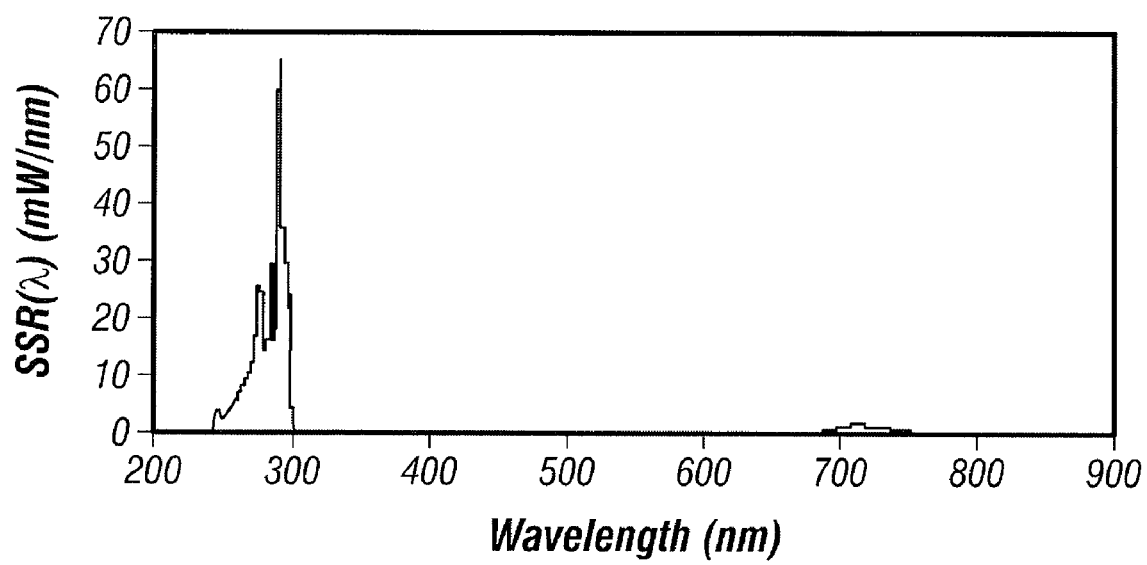

Any transparent material has a UV edge at a characteristic wavelength. The optical absorption for light with wavelengths in the neighborhood of this edge typically varies in an exponential fashion with increasing absorptivity for shorter wavelengths. A typical definition of the absorption edge is to take the wavelength at which the light has an absorption coefficient of 20 cm$^{-1}$. [L. Kovacs, G. Ruschhaupt, K. Polgar, G. Corradi, and M. Wohlecke, "Composition dependence of the ultraviolet absorption edge in lithium niobate," Applied Physics Letters 70(no. 21), 2801-2803 (1997)], incorporated herein by reference. If the absorption of the illuminating light is sufficiently large, the light refracted into the wafer 12 under investigation, and reflected or scattered from the backside is sufficiently attenuated so as not to interfere with the weakly scattered light from the front surface defects. For the example of congruent LN with absorption edge of 320 nm, the absorption coefficient at 315 nm is 50 cm$^{-1}$ and that at 310 nm exceeds 120 cm$^{-1}$ To ensure that the backsurface scatter does not interfere with the signal from front surface scratches, it is necessary that the spectral system response lies mostly below the absorption edge. In one embodiment that can be used for LN inspection, a combination of absorbing and thin film reflective filters can be inserted in the illumination path. The illumination response $t_{in}(\lambda)$ for this filter is shown in FIGS. 6(a) and 6(b) along with the spectral system response SSR assuming the source and camera spectral characteristics as shown in FIGS. 3 and 5(b). In this example, the filter defines a very sharp cutoff around 300 nm. There is some system response to wavelengths in the near IR. This light easily propagates to the backside of the surface of the wafer 12 where it can get scattered and consecutively imaged onto the detector array. However, this fraction of system response in the near IR is less than 10% of the overall system response which does not significantly decrease system performance. To ensure that scratches of a given material having UV cutoff wavelength $\lambda_{cutoff}$, over 90% of the spectral system response SSR should be at wavelengths below $\lambda_{cutoff}$–5 nm. This condition can be expressed as $$\int_0^{\lambda_{cutoff}-5nm} SSR(\lambda) > 0.90 \cdot \int_0^\infty SSR(\lambda)$$

EXAMPLE I

FIG. 1 shows the setup for the system 10 used in this example. The light output of a mercury high pressure lamp is collimated and illuminates the wafer placed on a stage that can be rotated. A filter consisting of two individual coated glass plates, the first a 2.1 mm thick colored UG11 glass (Schott Glass) with anti-reflection coatings, the second a quartz glass plate with thin film coating having very high reflectivity between 310 nm and 450 nm, is placed in the illumination path. The combined transmission through the filters is as shown in FIG. 4a. The camera is placed at a solid angle so that the specular reflection misses the aperture of the imaging lens. The camera had the response curve as shown in FIG. 5. A lithium niobate wafer, 0.5 mm thick was placed on the stage and the scattered image of the illuminated wafer surface was observed by the camera and recorded. Scratches were clearly visible as lines with higher intensity. As the wafer stage was rotated, the intensity of a particular scratch was observed to vary, depending on the relative orientation of the scratch with respect to the incoming light angle.

EXAMPLE II

FIG. 2 illustrates an alternative embodiment of the system 10 in Example 1. The light source is highly collimated, e.g. as a UV laser, imaged through a beam expander 117 onto the wafer surface. Filters may be inserted to block visible and IR light emanating from the plasma discharge. The specular reflection from the wafer surface is highly collimated and can be removed by two lenses and a beam block 113. Scattered light will leave the surface as different angles, not be blocked by the beam stop and be imaged onto the screen or the camera focal plane. The system works well, even for thin wafers, if the laser emission wavelength is shorter than $\lambda_{cutoff}$–5 nm.

EXAMPLE III

Tellurium dioxide (TeO$_2$, also called paratellurite) is often used as acousto-optic material because of its high figure of merit. Several crystal faces need to be polished, both for optical windows as well as for launching the acoustic wave. Typical geometries are rectangular pieces where one or more sides are polished. The polished faces of the acousto-optic cell 12 need to be inspected to ensure absence of scratches. The invention applies to inspecting such surfaces, even though the geometry is not a wafer, but a bulk crystal with one or more polished surfaces. Typical distances from the front surface to be inspected to the back surface, i.e. the surface parallel but opposite the front surface, is on the order of centimeters. This is larger than a typical thickness of a wafer, and the UV illumination beam 16 will be absorbed sufficiently in the crystal for material absorption values that are smaller than those for a wafer. For such thick substrates, we define the UV cutoff wavelength at a lower value of absorption coefficient. As compared to the LN wafer, the TeO2 cells are about 20 times thicker, and adequate reflection suppression is achieved for absorption coefficient values larger than about 1 cm$^{-1}$ For this material and application, the UV cutoff wavelength is therefore $\lambda_{cutoff}$=333 nm which is longer than if we had used the criterion 20 cm$^{-1}$ (324.6 nm). The system works well as long as the SSR has 90% of its intensity at wavelengths shorter than $\lambda_{cutoff}$–5 nm=328 nm. For the emission spectrum of the high pressure mercury lamp shown in FIG. 3, a UV filter with transmission below 328 nm will yield a UV illumination beam 16 that is 50% brighter than if the filter edge had been at 300 nm. This example shows that it is worthwhile to tailor the filter transmission function to the material to be inspected.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, the positioning of the LCD screen for the human interface may be varied so as to provide the best location for ergonomic use. The human interface may be a voice system that uses words to describe status or alarms related to device usage. Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method of detecting one or more scratches on a surface of a wafer made of a non-semiconductor material, comprising:
   providing a UV beam from a UV illumination source;
   causing a UV beam to be incident on a surface of a front surface of the wafer creating a reflected beam of scattering of the UV beam in response to scratches on a surface of the wafer, the UV beam being characterized that for scratches of a given material having a UV cutoff wavelength $\lambda_{cutoff}$, over 90% of the spectral system response SSR is at wavelengths below $\lambda_{cutoff}$–5 nm and expressed as:

$$\int_0^{\lambda_{cutoff}-5nm} SSR(\lambda) > 0.90 \cdot \int_0^\infty SSR(\lambda)$$

capturing the scattering from scratches with a UV camera.

2. The method of claim 1, wherein the non-semiconductor material is a piezo-electric material.

3. The method of claim 1, wherein the UV beam incident on the surface of the front surface of the wafer is in the range of 250 to 300 nm.

4. The method of claim 1, further comprising:
   providing a filter element in a path of the reflected beam to pass a UV beam in the range of 250 to 300 nm.

5. The method of claim 1, wherein the material is an acousto-optic material.

6. The method of claim 1, wherein the material is selected from TeO2 and sapphire.

7. The method of claim 1, wherein the wafer is made of a material with a UV cut-off in the range of 250 nm to 350 nm.

8. The method of claim 1, wherein the wafer is made of a material selected from at least one of, LN, LT, LBO, alpha quartz and the like.

9. The method of claim 1, wherein the reflected beam is a forward scattering beam.

10. The method of claim 1, wherein the UV illumination source is a mercury high pressure lamp and a filter that cuts out visible and near UV radiation at wavelengths longer than 300 nm, the filter being positioned between the mercy high pressure lamp and the UV camera.

11. The method of claim 1, further comprising:
using an optical lens to gather the scattering to the camera.

12. The method of claim 1, wherein image data acquisition and processing for scattering from scratches is done in a time period of less than 30 seconds.

13. The method of claim 1, wherein image data acquisition and processing for scattering from scratches is done in a time period of less than 30 seconds and more than a sub-second.

14. The method of claim 1, wherein the UV beam is absorbed by bulk material of the wafer, and the scattering is in response to scratches on a front surface of the wafer facing the UV beam regardless of conditions on a back surface of the wafer facing away from the UV beam.

15. The method of claim 1, wherein a diameter of the UV beam is at least equal to ½ of the wafer surface.

16. The method of claim 1, wherein the reflected beam is blocked by a beam stop, and the scattering is imaged onto a screen for detection by the UV camera.

17. The method of claim 16, wherein only the scattering is allowed to pass through the beam stop.

18. The method of claim 1, wherein the scattering is observed or captured at an angle of 30~80 degree from a front surface of the wafer facing the UV beam.

19. The method of claim 18, wherein only forward scattering is detected.

20. The method of claim 19, wherein only forward scattering is detected using a focus lens.

21. The method of claim 1, wherein the wafer has a size in the range of 100-200 mm.

22. A system for detecting scratch on a surface of a wafer made of a non-semiconductor material, comprising:
a UV source producing an output beam, the UV beam being characterized that for scratches of a given material having a UV cutoff wavelength $\lambda_{cutoff}$, over 90% of the spectral system response SSR is at wavelengths below $\lambda_{cutoff}$–5 nm and expressed as:

$$\int_0^{\lambda_{cutoff}-5nm} SSR(\lambda) > 0.90 \cdot \int_0^\infty SSR(\lambda)$$

a filter positioned between the UV source and a target wafer made of a non-semiconductor material, the UV output beam having a diameter equal to at least ½ of a surface area of the wafer;
a conversion lens;
a beam stop; and
a screen or camera.

23. The system of claim 22, wherein the screen is a fluorescent screen.

24. The system of claim 22, wherein the non-semiconductor material is a piezo-electric material.

25. The system of claim 22, wherein the output beam has a wavelength range of 250 to 300 nm.

26. The system of claim 22, further comprising:
A wafer chuck configured to hold a wafer to provide for at least one of wafer, rotation and tilt to provide from different wafer orientations.

27. A system for detecting scratch on a surface of a wafer made of a non-semiconductor material, comprising:
a UV source producing an output beam, the UV beam being characterized that for scratches of a given material having a UV cutoff wavelength $\lambda_{cutoff}$, over 90% of the spectral system response SSR is at wavelengths below $\lambda_{cutoff}$–5 nm and expressed as:

$$\int_0^{\lambda_{cutoff}-5nm} SSR(\lambda) > 0.90 \cdot \int_0^\infty SSR(\lambda)$$

a filter positioned between the UV source and a target wafer made of a non-semiconductor material, the UV output beam having a diameter equal to at least ½ of a surface area of the wafer;
a UV image lens; and
a UV camera with the image lens positioned in a front position relative to the UV camera.

28. The system of claim 27, wherein the non-semiconductor material is a piezo-electric material.

29. The system of claim 27, wherein the output beam has a wavelength range of 250 to 300 nm.

* * * * *